US00PP27053P2

(12) United States Plant Patent
Klemm et al.

(10) Patent No.: US PP27,053 P2
(45) Date of Patent: Aug. 9, 2016

(54) ***CALIBRACHOA* PLANT NAMED 'KLECA14270'**

(50) Latin Name: ***Calibrachoa* sp.**
Varietal Denomination: KLECA14270

(71) Applicant: Klemm+Sohn GmbH & Co. KG, Stuttgart (DE)

(72) Inventors: Nils Klemm, Stuttgart (DE); Anita Stöver, Ostfildern (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 14/544,528

(22) Filed: Jan. 15, 2015

(51) Int. Cl.
*A01H 5/02* (2006.01)

(52) U.S. Cl.
USPC ..... Plt./413

(58) Field of Classification Search
USPC ..... Plt./263.1, 413
See application file for complete search history.

*Primary Examiner* — Susan McCormick Ewoldt
*Assistant Examiner* — Karen Redden
(74) *Attorney, Agent, or Firm* — Bethany R. Roahrig; James M. Weatherly; Cochran Freund & Young, LLC

(57) ABSTRACT

A new *Calibrachoa* plant particularly distinguished by having a red flower color and a semi-trailing plant habit and form, is disclosed.

1 Drawing Sheet

Genus and species: *Calibrachoa* sp.
Variety denomination: 'KLECA14270'.

BACKGROUND OF THE NEW PLANT

The present invention comprises a new and distinct variety of *Calibrachoa*, botanically known as *Calibrachoa* sp., and hereinafter referred to by the variety name 'KLECA14270'. 'KLECA14270' originated from a controlled-cross between the proprietary female *Calibrachoa* variety 'CA-2011-0613' (unpatented) and the male *Calibrachoa* variety 'KLECA09172' (U.S. Plant Pat. No. 22,152).

In May 2011, two *Calibrachoa* parental lines, the female variety 'CA-2011-0613' and the male *Calibrachoa* variety 'KLECA09172' were crossed via a controlled cross in Stuttgart, Germany and seeds were obtained. The seeds were sown and plants were grown for evaluation. A plant line was selected in May 2012 which had a red flower color and subsequently named 'KLECA14270'. In May 2012, 'KLECA14270' was first vegetatively propagated by tip cuttings in Stuttgart, Germany. 'KLECA14270' was found to reproduce true to type in successive generations of asexual propagation via tip cuttings.

SUMMARY

The following are the most outstanding and distinguishing characteristics of this new variety when grown under normal horticultural practices in Stuttgart, Germany.

1. Red flower color; and
2. A semi-trailing plant habit and form.

DESCRIPTION OF THE PHOTOGRAPH

This new *Calibrachoa* plant is illustrated by the accompanying photograph which shows the flowers and foliage of the plant. The photograph is of a five-month-old plant grown outdoors in Stuttgart, Germany in July 2014. The colors shown are as true as can be reasonably obtained by conventional photographic procedures.

DESCRIPTION OF THE NEW VARIETY

The following detailed descriptions set forth the distinctive characteristics of 'KLECA14270'. The data which define these characteristics were collected from asexual reproductions carried out in Stuttgart, Germany. Data was collected on twelve week-old plants grown in Stuttgart, Germany in May of 2014. Color references are to The R.H.S. Colour Chart of The Royal Horticultural Society of London (R.H.S.), 5$^{th}$ edition (2007).

Classification:
- *Family*.—Solanaceae.
- *Species*.—*Calibrachoa* sp.
- *Common name*.—*Calibrachoa*.
- *Parentage*.—Female: Proprietary *Calibrachoa* 'CA-2011-0613' (unpatented). Male: *Calibrachoa* 'KLECA09172' (U.S. Plant Pat. No. 22,152).

Plant description:
- *Life cycle*.—Annual.
- *Form*.—Semi-trailing.
- *Habit*.—Semi-trailing.
- *Height (from soil line to top of foliage)*.—6.0 cm.
- *Spread*.—31.0 cm.

Propagation: Vegetatively propagated.
- *Type cuttings*.—Tip cuttings.
- *Time to produce a rooted cutting*.—3 weeks.

Stems:
- *Stem color*.—RHS 145A.
- *Pubescence*.—Absent.
- *Stem diameter*.—0.1 cm.
- *Stem length*.—15.0 cm. From soil line to first node: 1.7 cm. Total length: 17.0 cm.
- *Internode length*.—1.8 cm.

Leaves:
*Arrangement*.—Alternate, simple, sessile.
*Shape*.—Elliptic.
*Apex*.—Obtuse to slightly acute.
*Base*.—Attenuate.
*Margin*.—Entire.
*Surface*.—Smooth.
*Surface pubescence*.—Absent.
*Venation*.—Pinnate.
*Venation color*.—Upper surface: RHS 144B. Lower surface: RHS 145B.
*Length*.—2.9 cm.
*Width*.—0.9 cm.
*Color*.—Upper surface: RHS N137A. Lower surface: RHS 137D.
*Fragrance*.—Absent.

Flowers:
*Flowering habit*.—Single flowers.
*Flower type*.—Determinate inflorescence.
*Flowering requirements*.—A minimum of light sun is required.
*Duration of flowers*.—6 days.
*Corolla*.—Smooth texture.
*Shape*.—Trumpet shaped.
*Fragrance*.—Absent.

Flower buds:
*Surface*.—Smooth.
*Length*.—2.0 cm.
*Diameter*.—0.6 cm.
*Shape*.—Irregular to oblong.
*Color*.—RHS 186A.

Peduncle:
*Length*.—2.5 cm.
*Diameter*.—0.1 cm.
*Color*.—RHS 145A.
*Texture*.—Smooth.
*Anthocyanin color*.—RHS 200D.

Flower description:
*Flower depth*.—2.5 cm.
*Flower tube length*.—1.7 cm.
*Flower tube diameter*.—0.7 cm.
*Flower diameter*.—3.3 cm.
*Pedicel color*.—RHS 145A.
*Calyx*.—Funnel-shaped.
*Calyx texture*.—Smooth (both upper and lower surfaces).

Sepals:
*Shape*.—Lanceolate.
*Apex*.—Acute.
*Margin*.—Entire.
*Length*.—1.6 cm.
*Diameter*.—0.3 cm.
*Sepal color*.—Upper surface: RHS 143A. Lower surface: RHS 143C.

Petals:
*Shape*.—Heart-shaped.
*Length*.—1.3 cm.
*Diameter*.—1.6 cm.
*Apex*.—Obverse.
*Margin*.—Entire, weak undulation.
*Base*.—Open and fused in the tube.
*Pubescence*.—Absent.
*Lobe length*.—1.2 cm.
*Lobe width*.—1.6 cm.
*Color*.—Lobe color: Upper surface: RHS 53A; venation color RHS 59A. Lower surface: RHS 53D. Corolla tube color: Inner: RHS 7A; venation color RHS 187B. Outer: RHS 7D.
*Fragrance*.—Absent.

Reproductive organs:
*Stamen number*.—5. Anther color: RHS 13A. Filament color: RHS 2C. Pollen color: RHS 12A.
*Ovary*.—Placenta arrangement: Ovate. Pistil number: 1. Pistil length: 0.1 cm. Stigma color: RHS 144B. Style length: 1.0 cm. Style color: RHS 144D.

Fruit/seed set: Small quantity; description not available.
Disease/insect resistance: None observed.

COMPARISON WITH PARENTAL LINES AND KNOWN VARIETY

'KLECA14270' is distinguished from its parents as described in Table 1:

TABLE 1

Comparison with Parental Lines

| Trait | Variety 'KLECA14270' | Female parent 'CA-2011-0613' | Male Parent 'KLECA09172' |
|---|---|---|---|
| Flower color | RHS 53A | RHS 51A and RHS 53 | BRHS 46C |

'KLECA14270' is most similar to the *Calibrachoa* plant named 'KLECA13247', also known as MINIFAMOUS COMPACT 'Red' (unpatented). Differences between the two varieties are described in Table 2:

TABLE 2

Comparison with Similar Variety

| Trait | Variety 'KLECA14270' | Commercial line 'KLECA13247' |
|---|---|---|
| Flower color | RHS 53A | RHS 50A |
| Bud color | RHS 186A | RHS 60C |

We claim:

1. A new and distinct variety of *Calibrachoa* plant named 'KLECA14270' as illustrated and described herein.

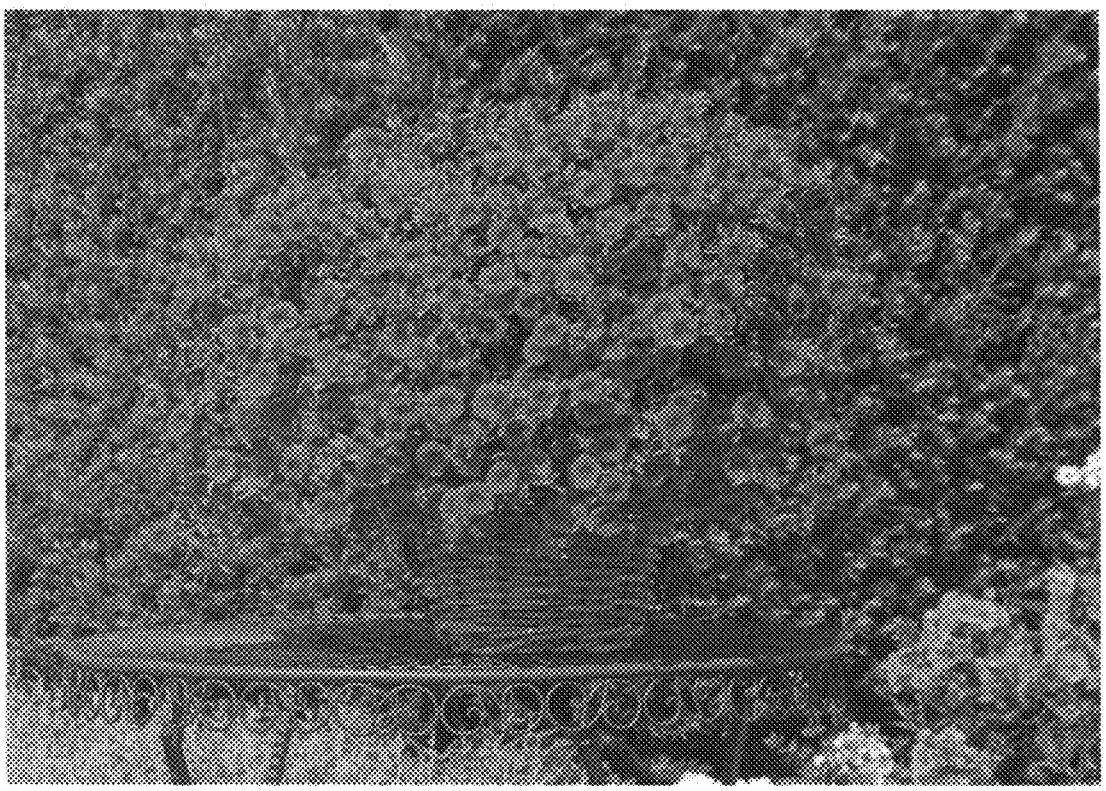

* * * * *